(12) United States Patent
Kelly et al.

(10) Patent No.: US 6,473,008 B2
(45) Date of Patent: Oct. 29, 2002

(54) SYSTEM FOR SAMPLING A DATA SIGNAL

(75) Inventors: Clifford Mark Kelly, Windham, NH (US); Marc Auerbach; Jonathan Fitch, both of Cupertino, CA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/777,345

(22) Filed: Feb. 6, 2001

(65) Prior Publication Data

US 2001/0045901 A1 Nov. 29, 2001

Related U.S. Application Data

(60) Provisional application No. 60/180,890, filed on Feb. 7, 2000.

(51) Int. Cl.$^7$ ............................................. H03M 7/04
(52) U.S. Cl. .......................... 341/61; 341/62; 341/63; 341/88; 341/100; 341/107; 341/155; 348/441; 348/445; 348/458; 348/264; 348/443
(58) Field of Search ................... 341/61, 50, 123, 341/144; 330/149

(56) References Cited

U.S. PATENT DOCUMENTS

| | | | |
|---|---|---|---|
| 3,023,277 A | 2/1962 | Mathews | |
| 4,146,743 A * | 3/1979 | Raynham | 341/70 |
| 4,555,669 A * | 11/1985 | Namiki | 330/149 |
| 4,827,259 A | 5/1989 | Murphy et al. | 341/123 |
| 5,229,668 A | 7/1993 | Hughes, Jr. et al. | 307/605 |
| 5,323,309 A | 6/1994 | Taylor et al. | 364/184 |
| 5,375,067 A | 12/1994 | Berchin | 364/487 |
| 5,400,371 A | 3/1995 | Natarajan | 375/122 |
| 5,621,805 A * | 4/1997 | Loh et al. | 381/119 |
| 5,625,359 A | 4/1997 | Wilson et al. | 341/143 |
| 5,633,634 A * | 5/1997 | Pawlowski | 341/61 |
| 5,645,068 A | 7/1997 | Mezack et al. | 128/670 |
| 5,677,738 A * | 10/1997 | Mizutani et al. | 348/445 |
| 5,797,399 A | 8/1998 | Morris et al. | 128/705 |
| 5,815,101 A | 9/1998 | Fonte | 341/123 |
| 5,903,482 A * | 5/1999 | Iwamura et al. | 341/61 |
| 5,907,295 A | 5/1999 | Lin | 341/61 |
| 5,936,438 A | 8/1999 | Whikehart et al. | 327/106 |
| 5,982,305 A * | 11/1999 | Taylor | 341/61 |
| 6,160,502 A * | 12/2000 | Ihm | 341/61 |
| 6,181,267 B1 * | 1/2001 | MacDonald et al. | 341/61 |
| 6,191,991 B1 * | 2/2001 | Wada | 365/219 |
| 6,326,999 B1 * | 12/2001 | Wise | 348/441 |

* cited by examiner

*Primary Examiner*—Michael Tokar
*Assistant Examiner*—Lam T Mai
(74) *Attorney, Agent, or Firm*—Alexander J. Burke

(57) ABSTRACT

A sampling system includes an input terminal for receiving a data signal having a signal component and possibly a noise component. A sampler samples the data signal at a sample rate set in responsive to a control signal. A noise detector detects the presence of a noise component, and if a noise component is detected, generates the control signal conditioning the sampler to sample the data signal at a first sample rate satisfying the Nyquist criterion for the data signal including the noise component, and otherwise generating the control signal conditioning the sampler to sample the data signal at a second data rate satisfying the Nyquist criterion for the data signal including only the signal component.

21 Claims, 2 Drawing Sheets

SYSTEM FOR SAMPLING A DATA SIGNAL

CROSS REFERENCE TO RELATED APPLICATIONS

This application expressly claims the benefit of earlier filing date and right of priority from the following co-pending patent application, which is assigned to the assignee of the present invention and have the same inventor: U.S. Provisional Application Serial No. 60/180,890, filed on Feb. 7, 2000, entitled "OPTIMIZED SAMPLING RATE." The above cited patent application is expressly incorporated in its entirety by reference.

FIELD OF THE INVENTION

The present invention relates to sampling methods and apparatus for low power applications.

BACKGROUND OF THE INVENTION

In medical applications, it is often required to monitor patient physiological parameters at all times, even when that patient cannot be connected to a patient monitor. This requires that a remote monitor, be carried by the patient. The monitor, in turn, is connected to electrodes placed at appropriate locations on the body, for example, electrocardiogram electrodes. The analog signals generated by these electrodes are received by the remote monitor. These signal are generally converted to digital samples which may either be stored in the monitor or transmitted via a telemetry link to a central monitor. In either event, the monitor must necessarily be battery powered, and consequently must be made to minimize power consumption. Such a monitor may also be subject to induced electrical noise.

Digital signal processing systems are well known, including those which operate on analog input signals. To process analog input signals, digital samples are taken of the analog signal by a sampler. The samples are then processed by the digital signal processing system. In most such systems, the sampling rate is fixed at a predetermined rate (see U.S. Pat. No. 5,229,668, issued Jul. 20, 1993 to Hughes, Jr. et al.; and U.S. Pat. No. 5,797,399, issued Aug. 25, 1998 to Morris et al.). Such systems also include sample rate converters, which receive samples at a first fixed rate, and produce corresponding samples at a second fixed rate (see U.S. Pat. No. 5,907,295, issued May 25, 1999 to Lin; U.S. Pat. No. 5,936,438, issued Aug. 10, 1999 to Whikehart et al.; and U.S. Pat. No. 5,982,305, issued Nov. 9, 1999 to Taylor). In other such systems, the sample rate is settable, and may be varied from one system implementation to another, or from processing one input signal to another, but once preset, the sample rate remains fixed at the preset rate (see U.S. Pat. No. 5,375,067, issued Dec. 20, 1994 to Berchin; U.S. Pat. No. 5,400,371, issued Mar. 21, 1995 to Natarajan; and U.S. Pat. No. 5,645,068, issued Jul. 8, 1997 to Mezack et al.).

Other systems can have their sample rate varied during use. Some such systems are used where a single analog input signal must be processed by different processing circuits which operate at respectively different sample rates. Systems of this type can vary the sample rate dynamically depending on the sample rate currently required by the processing circuitry (see U.S. Pat. No. 5,625,359, issued Apr. 29, 1997 to Wilson et al.).

In another system, samples are not taken uniformly, but at locations dependent on the input signal. In U.S. Pat. No. 3,023,277, issued Feb. 27, 1962 to Mathews, an input signal is sampled at positive and negative peak values of the input signal, whenever they occur, and samples representing those peak values are then further processed.

In yet another system, the sample rate is dynamically varied at times when more detail about the input signal is desired. For example, in systems adapted for remote operations under battery power, there is limited power, and usually limited storage for samples. In such systems, the sample rate is generally kept low. Only when some event of interest occurs, and a more detailed record of the input signal is desired, is the sample rate increased. Because it is well known that sampling at a higher rate takes more power than sampling at a lower rate, and because sampling at a higher rate is limited to only those times when it is needed, this technique conserves power. In addition, because fewer samples are taken at times when nothing of interest is occurring, the storage capacity, and thus the number of memory circuits required to store the samples, is reduced, further reducing the power required (see U.S. Pat. No. 4,827,259, issued May 2, 1989 to Murphy et al.; and U.S. Pat. No. 5,323,309, issued Jun. 21, 1994 to Taylor et al.)

It is also a well-known problem for input signals to include not only a signal component but also a noise component, both of which are converted to digital form when an analog signal is digitized by the sampler. Such a noise component usually has higher frequency content than the signal component. To remove noise at a higher frequency than the signal component, prior art systems fixed the sample rate so that it satisfied the Nyquist criterion for the highest frequency in, or expected to be in, the noise component and then filtered the resulting sample sequence to attenuate the noise component. However, as described above, increasing the sample rate of the sampler increases the power consumption of the digital processing system, and the storage requirements for the samples taken.

It is desirable to sample an analog input signal, including a signal component and possibly also a noise component, for processing in a digital signal processing system, in a manner which minimizes the noise present in the digital samples, while simultaneously minimizing the power consumption of the data acquisition system.

BRIEF SUMMARY OF THE INVENTION

The inventor realized that in some conditions, the input signal does not have a noise component. The inventor further realized that under these conditions, it is not necessary for the sampling rate to satisfy the Nyquist criterion for the (non-existent) noise component. Instead the sampling rate may be decreased to the point where it satisfies the Nyquist criterion for the signal component alone.

In accordance with principles of the present invention, a sampling system includes an input terminal for receiving a data signal having a signal component and possibly a noise component. A sampler samples the data signal at a sample rate set in responsive to a control signal. A noise detector detects the presence of a noise component, and if a noise component is detected, generates the control signal conditioning the sampler to sample the data signal at a first sample rate satisfying the Nyquist criterion for the data signal including the noise component, and otherwise generating the control signal conditioning the sampler to sample the data signal at a second data rate satisfying the Nyquist criterion for the data signal including only the signal component.

A sampling system according to the above invention is optimized to the signal actually being received. If the input signal contains only the signal component, with no noise component, then the sampling rate is decreased, thereby minimizing the power required. Only when a noise component is detected, the sampling rate is increased so that the noise component may be filtered out. In this manner, power is conserved to the extent possible.

DETAILED DESCRIPTION OF THE INVENTION

Figure 1:
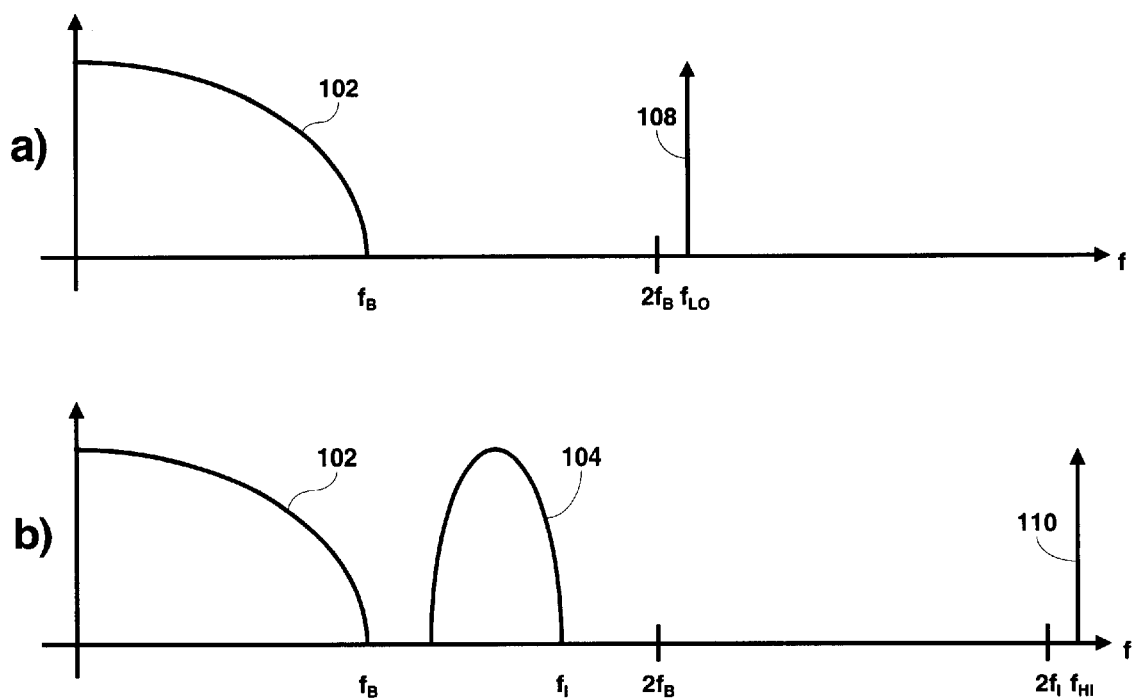
FIG. 1 is a spectral diagram useful in understanding the operation of the present invention.

FIG. 1 is a spectral diagram useful in understanding the operation of the present invention. In FIG. 1, the horizontal axis represents frequency and the vertical axis represents signal strength at that frequency. In FIG. 1, the spectrum of an analog input signal is illustrated. The input signal includes a signal component within a frequency band defined by the envelope 102, and a noise component within a frequency band defined by the envelope 104. FIG. 1a represents the condition when only the signal component 102 exists. As illustrated, the highest frequency associated with the signal component 102 is $f_B$. The Nyquist criterion for this signal component is satisfied if the sampling frequency is greater than or equal to twice the highest frequency $f_B$. This is illustrated in FIG. 1a as a sample clock signal 108 located at a frequency $f_{LO}$ greater than the frequency $2f_B$.

In FIG. 1b, a noise component 104 is also a component of the input signal. The noise component 104 has frequency band, defined by the envelope 104, which, in FIG. 1, is distinct from the frequency band of the signal component 102, though one skilled in the art will understand that the spectrum of the noise component 104 may overlap the spectrum 102 of the signal component. The highest frequency of the input signal is that of the noise component 104, which in FIG. 1b is $f_I$. In order to filter out the noise component 104, the Nyquist criterion for the input signal, including both the signal component 102 and noise component 104 must be satisfied. The Nyquist criterion is satisfied if the sampling frequency is greater than or equal to twice the highest frequency $f_I$ in the input signal. This is illustrated in FIG. 1b as a sample clock frequency 110 located at a frequency $f_{HI}$ greater than the frequency $2f_I$.

Figure 2:
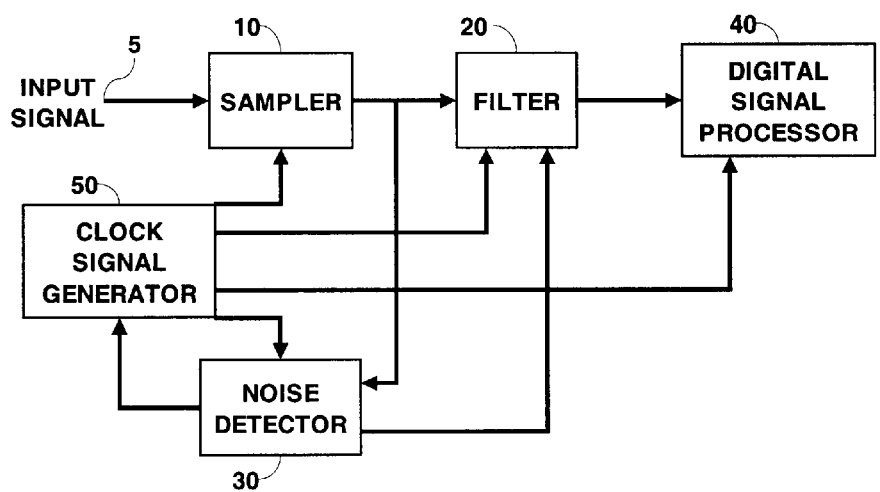
FIG. 2 is a block diagram of an embodiment of the present invention.

FIG. 2 is a block diagram of an embodiment of the present invention. In FIG. 2, an input terminal 5 is coupled to a source (not shown) of an analog input signal. The input terminal 5 receives the analog input signal and is coupled to an input terminal of a sampler 10. An output terminal of the sampler 10 is coupled to respective input terminals of a controllable filter 20 and a noise detector 30. An output terminal of the filter 20 is coupled to an input terminal of a digital signal processor (DSP) 40. A respective control output terminals of the noise detector 30 is coupled to corresponding control input terminals of a controllable clock signal generator 50 and the filter 20. Respective output terminals of the clock signal generator are coupled to corresponding clock signal input terminals of the sampler 10, the filter 20, the noise detector 30 and the digital signal processor 40.

In operation, the clock signal generator 50 supplies clock signals, at appropriate frequencies to the sampler 10, filter 20, noise detector 30 and DSP 40. The respective frequencies of these clock signals are adjusted in response to the control signal from the noise detector 30 in a manner to be described in more detail below. The analog input signal from input terminal 5, including a signal component and possibly a noise component, as illustrated in FIG. 1, is converted to digital samples representing the input signal in the sampler 10 at a rate set by the sample clock signal from the clock signal generator 50. These samples are filtered in the filter 20 to pass the signal component and attenuate the noise component in a manner to be described in more detail below. The characteristics of the filter 20 are adaptively set in response to the control signal from the noise detector 30, also in a manner to be described in more detail below. The filtered signal, with the noise component attenuated, is further processed by the DSP 40. The nature of this processing is not germane to the invention, and will not be described in detail. The processing frequency of the DSP is set by a DSP clock signal from the clock signal generator 50.

In the illustrated embodiment, the sampling system intermittently enters an analysis configuration, in which the presence and possibly the characteristic of a noise component is detected, in a manner described in more detail below. In this configuration, the noise detector 30 conditions the clock signal generator 50 to generate a sample clock signal at a high frequency, e.g. $f_{HI}$ as illustrated in FIG. 1b. The sample clock frequency ($f_{HI}$) is set to satisfy the Nyquist criterion for the highest frequency expected to be in any noise component which might be present. The samples from the sampler 10 are then analyzed to determine the frequency content of the input signal. More specifically, the frequency band which contains the noise component 104 is analyzed.

If the noise detector 30 detects no signal in that frequency band, then the analysis of the input signal stops, and the sampling system enters a low power configuration. In this configuration, the noise detector 30 conditions the clock signal generator 50 to generate a sample clock signal at the minimum sampling frequency $f_{LO}$, as illustrated in FIG. 1a. This sample clock frequency ($f_{LO}$) is set to satisfy the Nyquist criterion for the signal component 102 only. At the same time, the filter clock signal is similarly set to a minimum frequency, which in the illustrated embodiment is also $f_{LO}$. The noise detector 30 further conditions the filter 20 (e.g. setting tap coefficients and/or other filter parameters, in a known manner) to filter samples being produced at the sampling frequency $f_{LO}$ to a passband containing only the signal component 102, i.e. below frequency $f_B$. Reducing the sampling frequency of the sampler 10 and filter 20 reduces the power consumption of the sampling system illustrated in FIG. 1. It is also possible for the clock signal generator 50 to be conditioned by the noise detector 30 to generate a DSP clock signal at a minimum frequency as well. Processing filtered samples at this reduced clock rate will reduce the power consumption of the DSP 40 itself, further reducing the power consumption of the sampling system. The sampling system remains in this low power configuration until the next time the sampling system enters the analysis configuration, described above, in which the input signal is again checked for the presence of a noise component.

On the other hand, if the noise detector 30 detects a signal in the frequency band which contains the noise component 104, then the analysis of the input signal stops, and the sampling system enters a high sampling rate configuration. In this configuration the clock signal generator 50 is conditioned to set the frequency of the sample clock signal to the high frequency, e.g. $f_{HI}$ as illustrated in FIG. 1b. At the same time, the noise detector 30 conditions the clock signal generator 50 to generate a filter clock signal at a high frequency, which in the illustrated embodiment is also $f_{HI}$. The noise detector 30 further conditions the filter 20 to filter samples being produced at the high sampling frequency $f_{HI}$ to a passband containing only the signal component 102, i.e. below frequency $f_B$. In this manner, the noise component 104 is attenuated relative to the signal component 102. The noise detector also conditions the clock signal generator 50 to generate a high frequency clock signal for the DSP 40 so it may properly process the filtered samples from the filter 20 at the sampling frequency $f_{HI}$. This configuration permits sampling of the input signal containing a noise component at a sample rate high enough to permit the noise component to be attenuated at the expense of increased power consumption of the sampling system. The system remains in this high sampling rate configuration until the next time the sampling system enters the analysis configuration, described above, in which the input signal is again checked for the presence of a noise component.

In an alternative embodiment, in the analysis configuration if the noise detector 30 detects a signal in the frequency band which contains the noise component 104, a frequency $f_I$, representing the highest frequency currently in the noise component 104, is detected. The noise detector 30 then conditions the clock signal generator 50 to generate a sample clock signal having a frequency $f_S$ equal to $2f_I$, or just above it. The filter and DSP clock signals are set appropriately, as described above, and the filter 20 is also conditioned to filter samples at the sampling rate $f_S$ to a passband containing only the signal component 102, as before. This alternative embodiment permits sampling of the input signal containing a noise component at a sample rate high enough to permit the noise component to be filtered out, but at the minimum necessary sample rate, permitting power conservation to the maximum extent possible.

The analysis configuration, as described above, is entered intermittently, between low power and/or high sampling rate configurations. It may be entered periodically, i.e. at predetermined, substantially fixed time intervals; or at recurring, but not repetitive, time intervals; or at time intervals which depend on the presence and/or the strength of any detected noise component. It is preferred that the analysis configuration be entered sufficiently often so that any noise component may be detected and attenuated to prevent the accuracy of the samples taken from being unduly degraded; and conversely so that the absence of a noise component may be detected sufficiently quickly so that the sample rate, and thus the power consumption, may be minimized.

Figure 3:
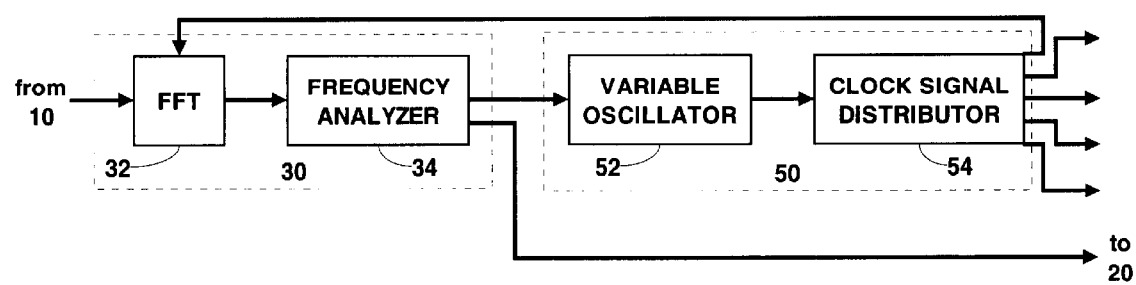
FIG. 3 is a more detailed block diagram of a portion of the sampling system illustrated in FIG. 2.

FIG. 3 is a more detailed block diagram of a portion of the sampling system illustrated in FIG. 2, more specifically including the noise detector 30 and clock signal generator 50. In FIG. 3, samples from the sampler 10 (of FIG. 2) are coupled to an input terminal of a fast Fourier transform (FFT) circuit 32. An output terminal of the FFT circuit 32 is coupled to an input terminal of a frequency analyzer 34. A first output terminal of the frequency analyzer is coupled to an input terminal of a variable frequency oscillator 52. A second output terminal of the frequency analyzer is coupled to the control input terminal of the filter 20. The combination of the FFT circuit 32 and frequency analyzer 34 are comprised within the noise detector 30, illustrated in FIG. 3 by a dashed line.

An output terminal of the variable frequency oscillator 52 is coupled to an input terminal of a clock signal distributor 54. Respective output terminals of the clock signal distributor 54 are coupled to corresponding clock signal input terminals of the sampler 10, filter 20, digital signal processor 40 (all of FIG. 2) and the FFT circuit 32 of the noise detector 30. The combination of the variable oscillator 52 and clock signal distributor 54 are comprised within the clock signal generator 50, illustrated in FIG. 3 by a dashed line.

In operation, the frequency analyzer 34 supplies a control signal to the variable oscillator 52, conditioning it to generate a master oscillator signal at a frequency dependent on the control signal. This master oscillator signal is used to control generation of the respective clock signals, e.g. the sample clock signal, filter clock signal, DSP clock signal, etc. These clock signals are then distributed to the corresponding elements in the sampling system, all in a known manner.

When the time occurs for the sampling system to enter the analysis configuration, to check for the presence of a noise component, as described above, the frequency analyzer 34 generates the control signal conditioning the variable oscillator 52 to produce a master oscillator signal at the maximum frequency. In response, the clock signal distributor 54 produces a sample clock signal at a frequency $f_{HI}$ which will satisfy the Nyquist criterion for the highest frequency expected in the noise component. The FFT circuit 32 is then activated, and begins to accumulate samples from the sampler 10 until the Fourier transform is complete. The FFT results are then analyzed by the frequency analyzer 34 to determine if a signal is present in the frequency band which contains the noise component. If no noise component is detected, then the frequency analyzer 34 conditions the oscillator 52 to produce a master oscillator signal at a minimum frequency: one that will produce a sample clock signal at a frequency of $f_{LO}$. The sampling system then enters the low power configuration. If, however, a noise component is detected, then the frequency analyzer 34 maintains the control signal, conditioning the oscillator 52 to maintain the maximum frequency and consequently to maintain the maximum sample frequency $f_{HI}$. The sampling system then enters the high sampling rate configuration.

In the alternative embodiment described above, the frequency analyzer 34 will analyze the resulting Fourier transform from the FFT circuit 32 to determine the highest frequency present in the noise component $f_I$ of the input signal. The frequency analyzer 34 then generates the control signal to condition the oscillator 52 to generate a master oscillator signal having a frequency which will cause the clock signal distributor 54 to generate a sample clock signal having a frequency $f_S$ which is equal to, or greater than, $2f_I$.

A remote patient monitor constructed according to the invention described above permits standalone monitoring of physiological signals with minimal power consumption, taking advantage of time periods when noise in the physiological signal is not present. Although illustrated as separate circuit elements, one skilled in the art will understand that the illustrated circuit elements may be fabricated as a processor executing a control program, in a known manner.

What is claimed is:

1. A system for sampling a data signal, comprising:
   an input terminal for receiving a data signal having a signal component and possibly a noise component;
   a sampler, coupled to the input terminal, for sampling the data signal at a sample rate set in response to a control signal; and
   a noise detector, coupled to the sampler, for detecting a noise component, and if a noise component is detected generating the control signal conditioning the sampler to sample the data signal at a first sample rate satisfying the Nyquist criterion for the data signal including the noise component, and otherwise generating the control signal conditioning the sampler to sample the data signal at a second data rate, satisfying the Nyquist criterion for the data signal including the signal component only wherein the second sample rate is a fixed sample rate greater than or equal to substantially twice the highest frequency of the signal component.

2. The system of claim 1 wherein:

the data signal comprises the signal component within a first frequency band, and the noise component within a second frequency band distinct from the first frequency band; and the noise detector comprises circuitry for detecting signals in the second frequency band, and if a signal is detected in the second frequency band, detecting a noise component.

3. The system of claim 2 wherein the noise detector comprises:

a frequency transform circuit, coupled to the sampler, for producing a signal representing the spectrum of the data signal; and an analyzer circuit, coupled to the transform circuit, for analyzing the spectrum representative signal in the second frequency band and if a signal is detected in the second frequency band, detecting a noise component.

4. The system of claim 3 wherein the frequency transform circuit comprises a discrete Fourier transform circuit.

5. The system of claim 4 wherein the discrete Fourier transform circuit comprises a fast Fourier transform circuit.

6. The system of claim 3 further comprising a filter, coupled to the sampler, for passing the first frequency band.

7. The system of claim 6 wherein the filter comprises a controllable filter, conditioned, in response to the noise detector, to process samples at the first sample rate to pass the first frequency band, and to process samples at the second sample rate to pass the first frequency band.

8. The system of claim 7 wherein:

the analyzer circuit further determines the highest frequency present in the noise component; and the noise detector generates the control signal conditioning the sampler to sample the data signal at the second sampling rate to satisfy the Nyquist criterion for the highest frequency present in the noise component.

9. The system of claim 8 wherein the controllable filter is conditioned, in response to the noise detector, to process samples at the second sampling rate, satisfying the Nyquist criterion for the higher frequency present in the noise component, to pass the first frequency band.

10. The system of claim 8 wherein the sampling rate is set to substantially twice the highest frequency in the noise component.

11. The system of claim 8 wherein the sampling rate is set equal to or greater than substantially twice the highest frequency in the noise component.

12. The system of claim 1 further comprising a controllable clock signal generator, coupled between the noise detector and the sampler, responsive to the noise detector, for generating a sample clock signal satisfying the Nyquist criterion for the data signal including the noise component if a noise component is detected and satisfying the Nyquist criterion for the data signal including the signal component only otherwise.

13. The system of claim 1 wherein the first sample rate is a fixed sample rate greater than or equal to substantially twice the highest expected frequency of the noise component.

14. The system of claim 1 wherein the first sample rate is greater than or equal to substantially twice the highest frequency in the noise component.

15. The system of claim 1 further comprising a filter coupled to the sampler, for filtering the sampled data signal to pass only the signal component.

16. The system of claim 1 further comprising a digital signal processor coupled to the sampler for processing the sampled data signal at a clock rate set in response to the control signal.

17. A method for sampling a data signal having a signal component and possibly a noise component, comprising the steps of:

sampling the data signal at a controllable sampling rate;

detecting the presence of a noise component in the data signal;

if a noise component is detected in the data signal, then controlling the sampling rate to a first rate which satisfies the Nyquist criterion for the data signal including the noise component, otherwise controlling the sampling rate to a second rate which satisfies the Nyquist criterion for the data signal including only the signal component.

18. The method of claim 17 further comprising the step of filtering the sampled signal to pass only the signal component.

19. The method of claim 17 further comprising the steps of:

processing the sampled data signal at a controllable processing clock rate;

if a noise component is detected in the data signal, then controlling the processing clock signal to a rate related to the first sampling rate, otherwise controlling the processing clock signal to a rate related to the second sampling rate.

20. The method of claim 17 wherein the detecting step further comprises the steps of:

detecting the highest frequency in the noise component; and controlling the sampling rate to a second rate which satisfies the Nyquist criterion for the highest frequency in the noise component.

21. A system for sampling a data signal, comprising:

an input terminal for receiving a data signal having a signal component and a noise component;

a sampler, coupled to the input terminal, for sampling the data signal at a sample rate set in response to a control signal; and a noise detector, coupled to the sampler, for detecting a noise component, and providing said control signal for adaptively adjusting a sampling rate of the system, wherein if a noise component of at least a threshold frequency is detected causing said system to operate at a first power level associated with a first sampling rate and otherwise causing said system to operate at a second power level associated with a second sampling rate, said second power level being substantially less than said first power level.

* * * * *